United States Patent

Suzuki et al.

[11] Patent Number: 5,703,085
[45] Date of Patent: Dec. 30, 1997

[54] XANTHINE DERIVATIVES

[75] Inventors: Fumio Suzuki, Mishima; Nobuaki Koike, Shizuoka; Junichi Shimada, Shizuoka; Joji Nakamura, Shizuoka; Shizuo Shiozaki, Fuji; Shigeto Kitamura, Machida; Shunji Ichikawa, Shizuoka; Hiroshi Kase, Koganei; Hiromi Nonaka, Shizuoka, all of Japan

[73] Assignee: Kyowa Hakko Kogyo Co., Ltd., Tokyo, Japan

[21] Appl. No.: 537,770

[22] PCT Filed: Feb. 23, 1995

[86] PCT No.: PCT/JP95/00267

§ 371 Date: Oct. 20, 1995

§ 102(e) Date: Oct. 20, 1995

[87] PCT Pub. No.: WO95/23148

PCT Pub. Date: Aug. 31, 1995

[30] Foreign Application Priority Data

Feb. 23, 1994 [JP] Japan ................... 6-025736

[51] Int. Cl.[6] .............. A61K 31/52; C07D 473/12; C07D 473/06; C07D 473/10
[52] U.S. Cl. .............. 514/263; 544/267; 544/271
[58] Field of Search ................. 544/271, 263

[56] References Cited

FOREIGN PATENT DOCUMENTS

| 0559893 | 9/1993 | European Pat. Off. . |
| 0565377 | 10/1993 | European Pat. Off. . |
| 0590919 | 4/1994 | European Pat. Off. . |
| 0607607 | 7/1994 | European Pat. Off. . |
| 0628311 | 12/1994 | European Pat. Off. . |
| 4325254 | 2/1994 | Germany . |

WO 25462 11/1994 WIPO .

OTHER PUBLICATIONS

Kato's Integrated English–Japanese Medical Dictionary (Nanzando, 1979) p. 757.
Jacobsen J. Med. Chem., vol. 36, No. 10 (1993) 1333–42.

*Primary Examiner*—Mark L. Berch
*Attorney, Agent, or Firm*—Fitzpatrick, Cella, Harper & Scinto

[57] ABSTRACT

The present invention relates to novel xanthine derivatives and pharmaceutically acceptable salts thereof, represented by Formula (I):

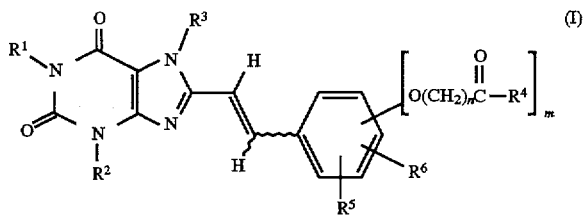

wherein $R^1$, $R^2$, and $R^3$ independently represent hydrogen, lower alkyl, lower alkenyl, or lower alkynyl, $R^4$ represents lower alkyl, or substituted or unsubstituted aryl, $R^5$ and $R^6$ independently represent hydrogen, lower alkyl, and lower alkoxy, or $R^5$ and $R^6$ are combined together to represent $-O-(CH_2)_p-O-$ (p is an integer of 1 to 3), n represents 0, 1, or 2, and m represents 1 or 2.

The compounds of the present invention have an adenosine $A_2$ receptor antagonistic activity, and are useful for the treatment or prevention of various kinds of diseases caused by hyperergasia of adenosine $A_2$ receptors (for example, Parkinson's disease, senile dementia, depression, asthma, and osteoporosis).

12 Claims, No Drawings

XANTHINE DERIVATIVES

TECHNICAL FIELD

The present invention relates to novel xanthine derivatives and pharmaceutically acceptable salts thereof which have adenosine $A_2$ receptor antagonistic activity and are useful for the treatment or prevention of various kinds of diseases caused by hyperergasia of adenosine $A_2$ receptors (for example, Parkinson's disease, senile dementia, depression, asthma, and osteoporosis).

BACKGROUND ART

It is known that adenosine exhibits neurotransmitter depressing activity [Eur. J. Pharmacol., 168, 285 (1989)], bronchospasmic activity [Br. J. Pharmacol., 100, 251(1990)], bone absorption promoting activity [Acta Physiol. Scand., 131, 287(1987)], and the like, via $A_2$ receptors. Therefore, adenosine $A_2$ receptor antagonists (hereinafter referred to as $A_2$-antagonists) are expected as therapeutic or preventive agents for various kinds of diseases caused by hyperergasia of adenosine $A_2$ receptors, for example, therapeutic agents for Parkinson's disease, antidementia agents, antidepressants, anti-asthmatic agents, and therapeutic agents for osteoporosis.

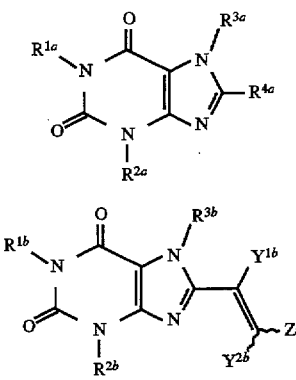

It is known that adenosine antagonistic activity is found in compounds represented by Formula (A) in which $R^{1a}$ and $R^{2a}$ independently represent methyl or propyl, $R^{3a}$ represents hydrogen, and $R^{4a}$ represents substituted or unsubstituted phenyl, aromatic heterocyclic group, cycloalkyl, styryl, or phenylethyl [J. Med. Chem., 34, 1431 (1991)]. Further, Japanese Published Examined Patent Application No. 26516/72 discloses, as cerebral stimulants, compounds represented by Formula (B) in which $R^{1b}$ and $R^{2b}$ independently represent methyl or ethyl, $R^{3b}$ represents methyl, $y^{1b}$ and $y^{2b}$ represent hydrogen, and $Z^b$ represents phenyl or 3,4,5-trimethoxyphenyl. WO92/06976 discloses, as compounds having an adenosine $A_2$ receptor antagonistic activity and therapeutic effects on asthma and osteoporosis, compounds represented by Formula (B) in which $R^{1b}$ and $R^{2b}$ independently represent hydrogen, propyl, butyl, or allyl, $R^{3b}$ represents hydrogen or lower alkyl, $y^{1b}$ and $y^{2b}$ independently represent hydrogen or methyl, and $Z^b$ represents substituted or unsubstituted phenyl, pyridyl, imidazolyl, furyl, or thienyl. Further, it is known that adenosine $A_2$ receptor antagonistic activity is found in compounds represented by Formula (B) in which $R^{1b}$ and $R^{2b}$ independently represent methyl, ethyl, propyl, or allyl, $R^{3b}$ represents hydrogen or methyl, $y^{1b}$ and $y^{2b}$ represent hydrogen, and $Z^b$ represents substituted or unsubstituted phenyl [J. Med. Chem., 36, 1333 (1993)]. Furthermore, among compounds represented by Formula (B) in which $R^{1b}$, $R^{2b}$ and $R^{3b}$ represent methyl, and $y^{1b}$ and $y^{2b}$ represent hydrogen, respectively, also known are a compound in which $Z^b$ represents phenyl (8-styryl caffeine) [Chem. Ber. 119, 1525 (1986)], and a compound in which $Z^b$ represents pyridyl, quinolyl, or methoxysubstituted or unsubstituted benzothiazolyl [Chem. Abst. 60, 1741h (1964)], although there is no description with regard to the pharmacological activity of any of these compounds.

DISCLOSURE OF THE INVENTION

The present invention relates to xanthine derivatives and pharmaceutically acceptable salts thereof represented by Formula (I):

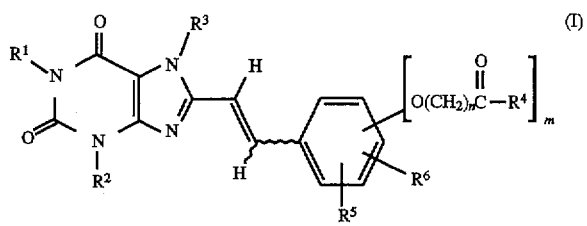

in which $R^1$, $R^2$, and $R^3$ independently represent hydrogen, lower alkyl, lower alkenyl, or lower alkynyl, $R^4$ represents lower alkyl, or substituted or unsubstituted aryl, $R^5$ and $R^6$ independently represent hydrogen, lower alkyl, and lower alkoxy, or $R^5$ and $R^6$ are combined together to represent —O—$(CH_2)$p—O— (p is an integer of 1 to 3), n represents 0, 1, or 2, and m represents 1 or 2.

Hereinafter, the compounds represented by Formula (I) are referred to as Compounds (I). The same shall apply to the compounds represented by other Formulae.

In the definitions of the groups in Formula (I), lower alkyl and the alkyl moiety of lower alkoxy mean straight-chain or branched alkyl group having 1 to 6 carbon atoms such as methyl, ethyl, propyl, isopropyl, butyl, isobutyl, sec-butyl, tert-butyl, pentyl, neopentyl and hexyl; lower alkenyl means straight-chain or branched alkenyl group having 2–6 carbon atoms such as vinyl, allyl, methacryl, crotyl, 3-butenyl, 2-pentenyl, 4-pentenyl, 2-hexenyl and 5-hexenyl; lower alkynyl means a straight-chain or branched alkynyl group having 2 to 6 carbon atoms such as ethynyl, propargyl, 2-butynyl, 3-butynyl, 2-pentynyl, 4-pentynyl, 2-hexynyl, 5-hexynyl and 4-methyl-2 pentynyl; and aryl represents phenyl or naphtyl.

Each of the substituents for aryl has 1 to 4 substitutions, and examples of which are substituted or unsubstituted lower alkyl, hydroxy, substituted or unsubstituted lower alkoxy, halogen, nitro, amino, lower alkylamino, di-lower alkylamino, benzyloxy, phenyl, and phenoxy. The lower alkyl, and the alkyl moiety of lower alkoxy, lower alkylamino and di-lower alkylamino have the same meanings as the lower alkyl defined above, and the halogen represents an atom of fluorine, chlorine, bromine, or iodine. Each of the substituents for lower alkyl and lower alkoxy has 1 to 3 substitutions, and examples of which are halogen, nitro, lower alkoxy and amino, wherein halogen and lower alkoxy have the same meanings as defined above.

The pharmaceutically acceptable salts of Compounds (I) include pharmaceutically acceptable acid addition salts, metal salts, ammonium salts, organic amine addition salts and amino acid addition salts.

The pharmaceutically acceptable acid addition salts include inorganic salts such as hydrochloride, sulfate, and phosphate, and organic salts such as acetate, maleate, fumarate, tartrate and citrate. The pharmaceutically acceptable metal salts include alkaline metal salts such as sodium salt and potassium salt, and alkali earth metal salts such as magnesium salt and calcium salt, aluminium salt, and zinc salt. The pharmaceutically acceptable ammonium salts include salts of ammonium and tetramethyl ammonium. The pharmaceutically acceptable organic amine addition salts include salts with morphorine and piperidine. The pharmaceutically acceptable amino acid addition salts include salts with lysine, glycine and phenylalanine.

A process for producing Compounds (I) is described below.

Compounds (I) are prepared according to the following reaction steps.

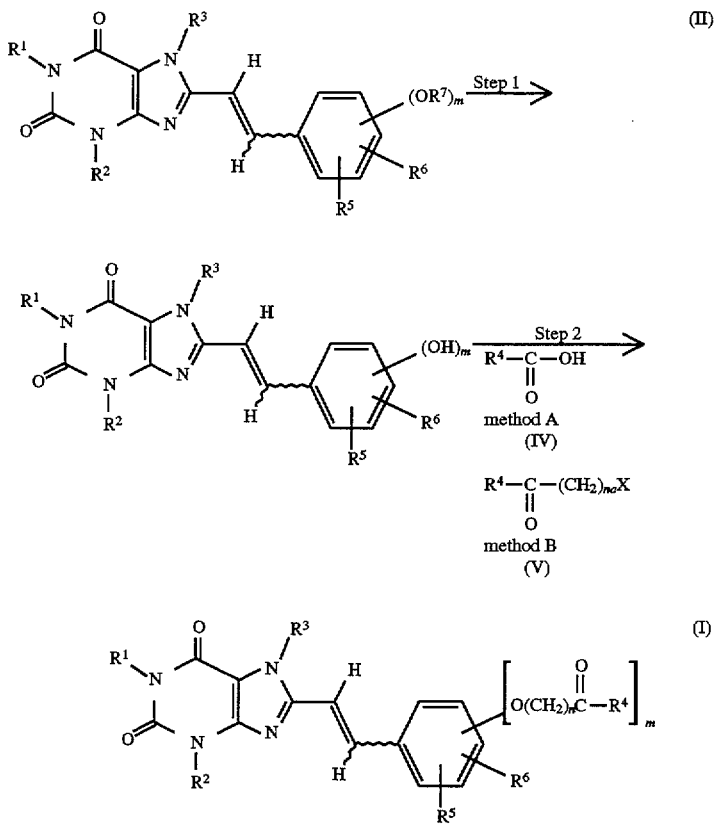

(wherein, $R^1$, $R^2$, $R^3$, $R^4$, $R^5$, $R^6$, n, and m have the same meanings as defined above, $R^7$ represents the lower alkyl as defined above, or methoxymethyl, X represents an atom of chlorine, bromine, or iodine, and na represents 1 or 2.)

Step 1:

Compounds (III) can be prepared by dealkylation of Compounds (II) obtained by known methods (e.g., WO92/06976). Examples of preferable dealkylation agent are boron tribromide and its dimethyldisulfide complex, boron trichloride, iodotrimethylsilane, sodium ethanethiolate, sodium benzenthiolate, gas of hydrogen chloride, hydrochloric acid and hydrobromic acid. The reaction solvent, varying depending on the dealkylation agent employed, is selected from aromatic hydrocarbons such as toluene and xylene, halogenohydrocarbons such as methylene chloride, chloroform and ethane dichloride, ethers such as dioxane and tetrahydrofuran, alcohols such as methanol and ethanol, dimethylformamide and acetic acid. The reaction is carried out at −30° to 140° C., and is completed in 10 minutes to 120 hours.

Step 2:
(Method A)

Compounds (I) wherein n is 0 can be obtained by reacting Compounds (III) with carboxylic acid (IV) or its reactive derivatives.

The reactive derivatives of Compounds (IV) include acid halides such as acid chloride and acid bromide, activated esters such as p-nitrophenyl ester and N-oxysuccinimide, acid anhydrides which are commercially available or which are produced using carbodiimide such as 3-(3-dimethylaminopropyl)-1-ethylcarbodiimide, diisopropylcarbodiimide and dicyclohexylcarbodiimide, and mixed acid anhydrides with monoethyl carbonate, monoisobutyl carbonate.

Generally, in case of using Compounds (IV), the reaction is carried out at 50° to 200° C. in the absence of solvent, and completed in 10 minutes to 5 hours.

When the reactive derivatives of Compounds (IV) are used in this step, the reaction can be carried out according to a method conventionally used in peptide chemistry. That is, Compounds (I), wherein n is 0, can be obtained by reacting Compounds (III) with the reactive derivatives of Compounds (IV) preferably in the presence of an additive or base. The reaction solvent is suitably selected from halogenohydrocarbons such as methylene chloride, chloroform and ethane dichloride, ethers such as dioxane and tetrahydrofuran, dimethylformamide, dimethylsulfoxide, water, etc. The additive includes 1-hydroxybenzotriazole. Pyridine, triethylamine, 4-dimethylaminopyridine, N-methylmorphorine, etc., are used as the base. The reaction is carried out at −80° to 50° C., and is completed in 0.5 to 24 hours. The reactive derivative, which is produced in the reaction system, may be used without isolation.

(Method B)

Compounds (I) wherein n is 1 or 2 can be obtained by reacting Compounds (III) with alkylation agent (V) in the presence of a base, if necessary.

The base includes alkaline metal carbonates such as sodium carbonate and potassium carbonate, alkaline metal hydrides such as sodium hydride, and alkaline metal alkoxides such as sodium methoxide and sodium ethoxide. As a reaction solvent, aromatic hydrocarbons such as toluene and xylene, ketones such as acetone and methylethylketone, dimethylformamide, dimethylsulfoxide, etc., are used. The reaction is carried out at 0° to 180° C. and is completed in 0.5 to 24 hours.

The desired compounds prepared according to the process described above can be isolated and purified by purification methods conventionally used in organic synthetic chemistry such as filtration, extraction, washing, drying, concentration, recrystallization and various kinds of chromatographies.

In the case where a salt of Compound (I) is desired and it is produced in the form of the desired salt, it can be subjected to purification as such. In the case where Compound (I) is produced in the free state and its salt is desired, Compound (I) is dissolved or suspended in a suitable solvent, followed by addition of an acid or a base to form a salt.

Compounds (I) can exist in the form of geometrical isomers such as an (E)-isomer and a (Z)-isomer, and the present invention covers all possible isomers including these geometrical isomers and mixtures thereof. In the case where separation between an (E)-isomer and a (Z)-isomer is desired, they can be isolated and purified by fractionation methods, for example, fractional crystallization, fractional precipitation, fractional dissolution, and various kinds of chromatographies.

Compounds (I) and pharmaceutically acceptable salts thereof may exist in the form of an adduct with water or various kinds of solvents, which are also within the scope of the present invention.

Specific examples of Compounds (I) are shown in Table 1.

TABLE 1

| Compound | $R^1$ | $R^2$ | Z |
|---|---|---|---|
| 1 | $-(CH_2)_2CH_3$ | $-(CH_2)_2CH_3$ | phenyl with $OCOCH_3$, $OCOCH_3$ |
| 2 | $-(CH_2)_2CH_3$ | $-(CH_2)_2CH_3$ | phenyl with $OCOC_6H_5$, $OCOC_6H_5$ |
| 3 | $-(CH_2)_2CH_3$ | $-(CH_2)_2CH_3$ | phenyl with $OCOCH_3$, $OCH_3$ |
| 4 | $-(CH_2)_2CH_3$ | $-(CH_2)_2CH_3$ | phenyl with $OCH_3$, $OCOCH_3$ |
| 5 | $-CH_2CH_3$ | $-CH_2CH_3$ | phenyl with $OCH_3$, $OCOCH_3$ |
| 6 | $-(CH_2)_2CH_3$ | $-(CH_2)_2CH_3$ | phenyl with $OCH_3$, $OCOC_6H_5$ |

TABLE 1-continued
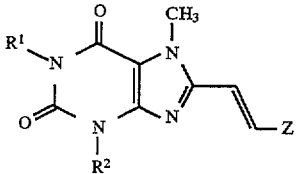
| Compound | R¹ | R² | Z |
|---|---|---|---|
| 7 | —CH₂CH₃ | —CH₂CH₃ | 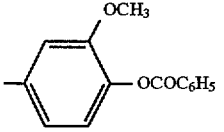 |
| 8 | —CH₂CH₃ | —CH₂CH₃ | 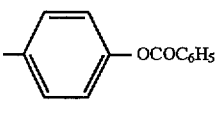 |
| 9 | —(CH₂)₂CH₃ | —(CH₂)₂CH₃ | 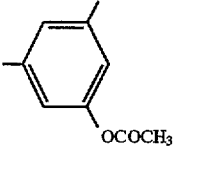 |
| 10 | —CH₂CH₃ | —CH₂CH₃ | 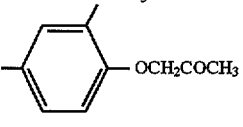 |
| 11 | —CH₂CH₃ | —CH₂CH₃ | 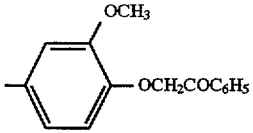 |
| 12 | —CH₂CH₃ | —CH₂CH₃ | 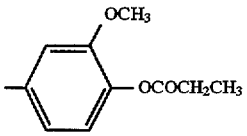 |
| 13 | —CH₂CH₃ | —CH₂CH₃ | 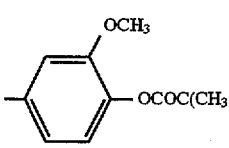 |
| 14 | —CH₂CH₃ | —CH₂CH₃ | 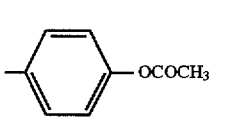 |
| 15 | —CH₂CH=CH₂ | —CH₂CH=CH₂ | 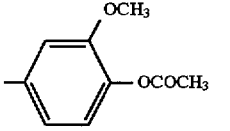 |

TABLE 1-continued
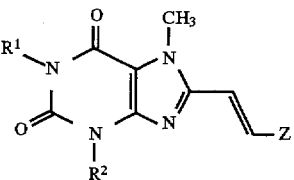
| Compound | R¹ | R² | Z |
|---|---|---|---|
| 16 | —CH₂CH₃ | —CH₂CH₃ | 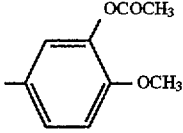 |
| 17 | —CH₂CH₃ | —CH₂CH₃ | 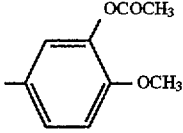 |
| 18 | —CH₂CH₃ | —CH₂CH₃ | 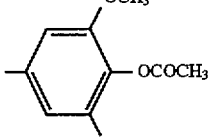 |
| 19 | —CH₂CH=CH₂ | —CH₂CH=CH₂ | 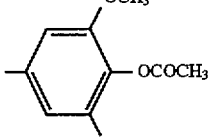 |
| 20 | —CH₂CH=CH₂ | —CH₂CH=CH₂ | 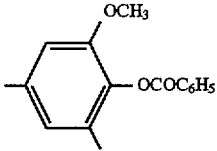 |
| 21 | —CH₂CH₃ | —CH₂CH₃ | 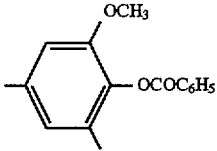 |
| 22 | —CH₂CH₃ | —CH₂CH₃ | 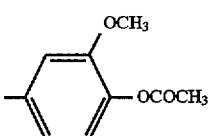 |
| 23 | —CH₂CH₃ | —CH₂CH₃ | 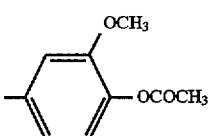 |

TABLE 1-continued

[Structure: imidazole-fused xanthine core with R¹-N, R²-N, N-CH₃, and 2-vinyl-Z substituent]

| Compound | R¹ | R² | Z |
|---|---|---|---|
| 24 | —CH₂CH₃ | —CH₂CH₃ | phenyl with OCH₃ and OCOC₆H₅ |
| 25 | —CH₂CH₃ | —CH₂CH₃ | phenyl with H₃COCO and OCH₃ |
| 26 | —CH₂CH₃ | —CH₂CH₃ | phenyl with H₃COCO and OCOCH₃ |
| 27 | —CH₂CH₃ | —CH₂CH₃ | phenyl with methylenedioxy (O–CH₂–O) and OCOCH₃ |

The pharmacological activities of Compounds (I) are shown below by test examples.

TEST EXAMPLE 1

Adenosine Receptor Antagonistic Activity (Adenosine $A_2$ Receptor Binding Test)

The test was conducted according to the method of Bruns et al. [Mol. Pharmacol., 29, 331 (1986)] with slight modification.

Corpus striatum of a rat was suspended in ice-cooled 50 mM Tris (hydroxymethyl) aminomethane hydrochloride (Tris HCl) buffer (pH 7.7) by using Polytron homogenizer (manufactured by Kinematica Co.). The suspension was centrifuged (50,000×g, 10 minutes), and the precipitate was suspended again in the same amount of 50 mM Tris HCl buffer. The suspension was centrifuged under the same conditions, and the final precipitate was suspended in 50 mM Tris HCl buffer [containing 10 mM magnesium chloride and 0.02 unit/mg tissue of adenosine deaminase (manufactured by Sigma Co.)] to give a tissue concentration of 5 mg (wet weight)/ml.

To 1 ml of the tissue suspension thus prepared were added 50 μl of tritium labeled CGS 21680 {³H-2-[p-(2-carboxyethyl) phenethylamino]-5'-(N-ethylcarboxamide)-adenosine: 40 Ci/mmol; manufactured by New England Nuclear Co. [J. Pharmacol. Exp. Ther., 251, 888 (1989)]} (final concentration: 4.0 nM) and 50 μl of a test compound.

The resulting mixture was allowed to stand at 25° C. for 120 minutes and then rapidly filtered by suction through a glass fiber filter (GF/C; manufactured by Whatman Co.). The filter was immediately washed three times with 5 ml each of ice-cooled 50 mM Tris HCl buffer, and transferred to a vial, and a scintillator (EX-H; manufactured by Wako Pure Chemical Industries, Ltd.) was added thereto. The radioactivity on the filter was determined with a liquid scintillation counter (manufactured by Packard Instrument Co.).

The inhibition rate of the test compound against the binding of $A_2$ receptors (³H-CGS 21680 binding) was calculated by the following equation:

$$\text{Inhibition Rate (\%)} = \left(1 - \frac{[B]-[N]}{[T]-[N]}\right) \times 100$$

[Notes]
B: Amount of the binding in the presence of the test compound.
T: Amount of the total binding.
N: Amount of the nonspecific binding.

Amount of the total binding means the amount of radioactivity of ³H-CGS 21680 bound in the absence of the test compound. Amount of the nonspecific binding means the amount of radioactivity of ³H-CGS 21680 bound in the presence of 100 μM cyclopentyladenosine (CPA; manufactured by Sigma Co.). Amount of the binding in the presence of the test compound means the amount of radioactivity of $^3$H-CGS 21680 bound in the presence of the test compound at various levels of concentrations.

The results are shown in Table 2.

TABLE 2

| Compd. | A$_2$ Receptor Inhibition Rate (%) | |
|---|---|---|
| | $10^{-7}$M | $10^{-6}$M |
| 1 | 89 | 93 |
| 3 | 61 | 96 |
| 4 | 94 | 98 |
| 5 | 91 | 100 |
| 6 | 81 | 96 |
| 7 | 87 | 97 |
| 9 | 88 | 96 |
| 12 | 86 | 96 |
| 14 | 86 | 93 |
| 15 | 85 | 91 |
| 16 | 81 | 96 |
| 17 | 80 | 97 |
| 18 | 82 | 97 |
| 19 | 91 | 96 |
| 21 | 81 | 96 |
| 22 | 92 | 99 |
| 23 | 90 | 101 |
| 25 | 95 | 101 |
| 26 | 75 | 101 |

Compounds (I) and pharmaceutically acceptable salts thereof exhibit a potent adenosine A$_2$ receptor antagonistic activity. Thus, they are effective against various kinds of diseases caused by hyperergasia of adenosine A$_2$ receptors (for example, Parkinson's disease, senile dementia, asthma, and osteoporosis).

TEST EXAMPLE 2

Effect on Haloperidol-Induced Catalepsy

Parkinson's disease is a clinical syndrome caused by degeneration and cell death of nigrostriatal dopaminergic neurons. Administration of haloperidol (dopamine D$_1$/D$_2$ antagonist) induces catalepsy resulting from the blockade of postsynaptic dopamine D$_2$ receptors. It is generally accepted that this haloperidol-induced catalepsy is a classical model to reproduce drug-induced Parkinson's disease [Eur. J. Pharmacol., 182, 327 (1990)].

The experiment was carried out using several groups of 5-week-old male ddY mice (weighing 22 to 24 g, Japan SLC), each group consisting of 5 or 10 mice. Haloperidol (manufactured by Janssen Pharmaceutica) was suspended in 0.3% CMC and imtraperitoneally administered to each mouse at a dose of 1.0 mg/kg. A test compound was suspended in injectable distilled water (manufactured by Otsuka Pharmaceutical Co., Ltd.) after adding Tween 80 [polyoxyethylene (20) sorbitan monooleate]. L-DOPA (manufactured by Kyowa Hakko Kogyo Co., Ltd.) and benserazide hydrochloride (manufactured by Kyowa Hakko Kogyo Co., Ltd.) were suspended in 0.3% CMC. One hour after the intraperitoneal administration of haloperidol, the suspension containing the test compound or the suspension containing no test compound [injectable distilled water (manufactured by Otsuka Pharmaceutical Co., Ltd.) containing Tween 80; control] were orally administered to the separate groups of the mice (0.1 ml per 10 g of body weight). One hour after the administration of the test compound, the forelimbs of each mouse and subsequently the hindlimbs of the same mouse were placed on a 4.5 cm-high, 1.0 cm-wide bar and catalepsy was estimated. All of the test compounds were orally administered at a dose of 10 mg/kg, and L-DOPA (100 mg/kg) and benserazide (25 mg/kg) were intraperitoneally administered together as a control. The catalepsy score and the standard of judgment are shown below.

| Score | | Duration of the category | |
|---|---|---|---|
| 0: | | forelimbs | less than 5 seconds |
| | | hindlimbs | less than 5 seconds |
| 1: | | forelimbs | from 5 (inclusive) to 10 (exclusive) seconds |
| | | hindlimbs | less than 5 seconds |
| 2: | | forelimbs | 10 seconds or more |
| | | hindlimbs | less than 5 seconds |
| 3: | (1) | forelimbs | from 5 (inclusive) to 10 (exclusive) seconds |
| | | hindlimbs | from 5 (inclusive) to 10 (exclusive) seconds |
| | or (2) | forelimbs | less than 5 seconds |
| | | hindlimbs | 5 seconds or more |
| 4: | (1) | forelimbs | 10 seconds or more |
| | | hindlimbs | from 5 (inclusive) to 10 (exclusive) seconds |
| | or (2) | forelimbs | from 5 (inclusive) to 10 (exclusive) seconds |
| | | hindlimbs | 10 seconds or more |
| 5: | | forelimbs | 10 seconds or more |
| | | hindlimbs | 10 seconds or more |

The effect of the compounds was evaluated by the total of the catalepsy scores of 5 or 10 mice in each group (25 or 50 points at the maximum). The groups wherein the total score was not more than 20 or 40 points were estimated to be effective. The number of the animals showing remission against catalepsy is the number of the mice for which the catalepsy score was not more than 4 points in 5 or 10 mice. The remission rate against catalepsy shows the rate of decrease in the total score based on that of the control group.

The results are shown in Table 3.

TABLE 3

| Compound | Number of Animals | Total Score | Number of Animals Showing Remission | Remission Rate (%) |
|---|---|---|---|---|
| 0.3% Tween 80 (Control) | 5 | 25 | 0 | 0 |
| L-DOPA + benserazide | 5 | 18 | 4 | 28 |
| 4 | 5 | 3 | 5 | 88 |
| 5 | 5 | 2 | 5 | 92 |
| 6 | 5 | 9 | 5 | 64 |
| 7 | 5 | 14 | 3 | 44 |
| 12 | 10 | 10 | 10 | 80 |
| 13 | 10 | 14 | 9 | 72 |
| 14 | 10 | 11 | 10 | 78 |
| 17 | 10 | 30 | 7 | 40 |
| 18 | 10 | 30 | 7 | 40 |

TEST EXAMPLE 3

Effect on Clonidine-Induced Aggressive Behavior

The enhancement effect of the test compounds on the aggressive behavior induced by intraperitoneal administration of clonidine [Eur. J. Pharmacol., 29, 374 (1968)] was investigated.

The experiment was performed using several groups of male ddY mice weighing 20 to 25 g (Japan SLC), each group consisting of two mice. A test compound was suspended in injectable distilled water (manufactured by Otsuka Pharmaceutical Co., Ltd.) after adding Tween 80. Clonidine hydrochloride (manufactured by Sigma Co.) was dissolved in physiological saline solution (manufactured by Otsuka Pharmaceutical Co., Ltd.). The suspension containing the test compound and the suspension containing no test compound (control) were orally administered to the separate groups of the mice (0.1 ml per 10 g of body weight). Sixty minutes after the oral administration of the test compound, clonidine hydrochloride (20 mg/kg) was intraperitoneally administered. The number of biting attacks during the 30 minutes immediately after the clonidine treatment was counted. The effect of the compounds was evaluated by comparing the number of biting attacks of the test compound-administered groups with that of control groups (significance test: Student' t-test).

The results are shown in Table 4.

TABLE 4

| Compd. | Dose (mg/kg, po) | Number of the Biting Attacks (mean ± S.E.M.) | | Ratio of Attacks: Test Compd.-Treated Group/ Control Group |
|---|---|---|---|---|
| | | Control Group (Number of Animals) | Test Compound-Treated Group (Number of Animals) | |
| 4 | 2.5 | 4.3 ± 1.9 (15) | 47.4 ± 11.1** (15) | 11.0 |
| 5 | 0.63 | 3.9 ± 1.5 (15) | 19.1 ± 6.6* (15) | 4.9 |
| 6 | 10 | 2.3 ± 1.3 (15) | 36.8 ± 10.8** (15) | 16.0 |
| 12 | 2.5 | 1.9 ± 1.3 (10) | 38.5 ± 8.4** (10) | 20.3 |
| 13 | 2.5 | 2.4 ± 1.1 (10) | 24.3 ± 6.6** (10) | 10.1 |
| 14 | 0.63 | 5.2 ± 1.6 (15) | 21.4 ± 7.4* (15) | 4.1 |

*p <0.05; **p <0.01

Compounds (I) and pharmaceutically acceptable salts thereof can be administered as they are, or in the form of various pharmaceutical compositions. The pharmaceutical compositions in accordance with the present invention can be prepared by uniformly mixing an effective amount of Compound (I) or a pharmaceutically acceptable salt thereof, as an active ingredient, with pharmaceutically acceptable carriers. It is desired that such pharmaceutical compositions are prepared in a unit dose form suitable for oral administration or administration through injection.

For preparing a pharmaceutical composition for oral administration, any useful pharmaceutically acceptable carrier may be used. For example, liquid preparations for oral administration such as a suspension and syrup can be prepared using water, sugars such as sucrose, sorbitol and fructose, gycols such as polyethylene glycol and propylene glycol, oils such as sesame oil, olive oil and soybean oil, preservatives such as p-hydroxybenzoates, flavors such as strawberry flavor and peppermint, and the like. Powders, pills, capsules, and tablets can be prepared using excipients such as lactose, glucose, sucrose, and mannitol, disintegrating agents such as starch and sodium alginate, lubricants such as magnesium stearate and talc, binders such as polyvinyl alcohol, hydroxypropyl cellulose, and gelatin, surfactants such as fatty acid esters, plasticizers such as glycerin, and the like. Tablets and capsules are the most useful oral unit dose forms because of the readiness of administration. For preparing tablets and capsules, solid pharmaceutical carriers are used.

Injectable preparations can be prepared using carriers such as distilled water, a salt solution, a glucose solution or a mixture of a salt solution and a glucose solution. The preparations can be prepared in the form of a solution, suspension, or dispersion according to a conventional method using a suitable solubilizing agent and suspending agent.

Compounds (I) and pharmaceutically acceptable salts thereof can be administered orally in the said dosage forms or parenterally as injections. The effective dose and the administration schedule vary depending upon the mode of administration, the age, body weight, and the condition of a patient, etc. Generally, however, Compounds (I) or pharmaceutically acceptable salts thereof are administered in a daily dose of 0.01 to 25 mg/kg in 3 to 4 parts.

In addition, Compounds (I) may also be administered by inhalation in the form of an aerosol, fine powders or a spray solution. In the case of aerosol administration, the compound of the present invention is dissolved in an appropriate pharmaceutically acceptable solvent such as ethyl alcohol or a combination of solvents containing ethyl alcohol, and the resulting solution is mixed with a pharmaceutically acceptable propellant.

Certain embodiments of the present invention are illustrated in the following examples, reference examples, and preparation examples.

EXAMPLE 1

(E)-8-(3,4-Diacetoxystyryl)-7-methyl-1,3-dipropylxanthine (Compound 1)

Compound a (350 mg, 0.910 mmol) obtained in Reference Example 1 was dissolved in 7 ml of pyridine, and acetic anhydride (0.51 ml, 5.405 mmol) was added thereto, followed by stirring at room temperature for 5 hours. Water was added to the reaction mixture, and the resulting precipitate was collected by filtration. The obtained crude product was recrystallized from hexane/ethyl acetate to give 294 mg (69% yield) of Compound 1 as pale yellow crystals.

Melting Point:229.4°–230.2° C. Elemental Analysis:$C_{24}H_{28}N_4O_6$ Calcd. (%):C 61.53, H 6.02, N 11.96 Found (%):C 61.56, H 6.05, N 11.97 IR(KBr)vmax (cm$^{-1}$) :1697, 1657, 1509, 1214. NMR (270 MHz; CDCl$_3$) δ(ppm) :7.73(1H, d, J=15.5 Hz), 7.47–7.43(2H, m), 7.24(1H, d, J=8.3 Hz), 6.84(1H, d, J=15.5 Hz), 4.08(2H, t, J=7.6 Hz), 4.05(3H, s), 3.98(2H, q, J=7.6 Hz), 2.32(3H, s), 2.31(3H, s), 1.83(2H, m), 1.69(2H, m), 1.00(3H, t, J=7.6 Hz), 0.97(3H, t, J=7.6 Hz).

EXAMPLE 2

(E)-8-(3,4-Dibenzoyloxystyryl)-7-methyl-1,3-dipropylxanthine (Compound 2)

Compound a (500 mg, 1.301 mmol) obtained in Reference Example 1 was dissolved in 10 ml of pyridine, and benzoyl chloride (0.60 ml, 5.169 mmol) was added thereto under ice-cooling, followed by stirring at room temperature for 3.5 hours. Ice and water were added to the reaction mixture, and the resulting precipitate was collected by filtration. The obtained crude product was recrystallized from ethyl acetate to give 663 mg (86% yield) of Compound 2 as white crystals.

Melting Point:230.8°–231.1° C. Elemental Analysis:$C_{34}H_{32}N_4O_6 \cdot 0.2 H_2O$ Calcd. (%):C 68.49, H 5.48, N 9.40 Found (%):C 68.50, H 5.40, N 9.35 IR(KBr)vmax (cm$^{-1}$):1747, 1694, 1654, 1440, 1242. NMR (270 MHz; CDCl$_3$) δ(ppm):8.10–8.05(4H, m), 7.81(1H, d, J=15.5 Hz), 7.76–7.36(9H, m), 6.91(1H, d, J=15.5 Hz), 4.14–3.96(4H, m), 4.07(3H, s), 1.91–1.63(4H, m), 1.01(3H, t, J=7.6 Hz), 0.97(3H, t, J=7.6 Hz).

EXAMPLE 3

(E)-8-(3-Acetoxy-4-methoxystyryl)-7-methyl-1,3-dipropylxanthine (Compound 3)

Substantially the same procedure as in Example 1 was repeated using 88 mg (0.221 mmol) of Compound b obtained in Reference Example 2. The obtained crude product was recrystallized from hexane/ethyl acetate to give 38 mg (39% yield) of Compound 3 as pale brown crystals.

Melting Point:200.8°–201.8° C. Elemental Analysis:$C_{23}H_{28}N_4O_5$ Calcd. (%):C 62.72, H 6.40, N 12.72 Found (%):C 62.41, H 6.50, N 12.52 IR(KBr)vmax (Cm$^{-1}$):1699, 1655, 1516, 1439, 1273. NMR (270 MHz; $CDCl_3$) δ(ppm):7.70(1H, d, J=15.8 Hz), 7.41(1H, dd, J=8.6, 2.0 Hz), 7.32(1H, d, J=2.0 Hz), 6.98(1H, d, J=8.6 Hz), 6.75(1H, d, J=15.8 Hz), 4.12–3.95(4H, m), 4.04(3H, s), 3.88(3H, s), 2.34(3H, s), 1.90–1.65(4H, m), 1.00(3H, t, J=7.3 Hz), 0.96 (3H, t, J=7.3 Hz)

EXAMPLE 4

(E)-8-(4-Acetoxy-3-methoxystyryl)-7-methyl-1,3-dipropylxanthine (Compound 4)

Substantially the same procedure as in Example 1 was repeated using 500 mg (1.255 mmol) of Compound e obtained in Reference Example 5. The obtained crude product was recrystallized from hexane/ethYl acetate to give 428 mg (77% yield) of Compound 4 as pale yellow crystals.

Melting Point:179.4°–181.3° C. Elemental Analysis:$C_{23}H_{28}N_4O_5$ Calcd. (%):C 62.72, H 6.40, N 12.72 Found (%):C 62.51, H 6.43, N 12.98 IR(KBr)vmax (cm$^{-1}$):1759, 1692, 1660, 1542, 1509, 1438. NMR (270 MHz; $CDCl_3$) δ(ppm):7.75(1H, d, J=15.8 Hz), 7.20(1H, dd, J=8.2, 1.7 Hz), 7.13(1H, d, J=1.7 Hz), 7.08(1H, d, J=8.2 Hz), 6.84(1H, d, J=15.8 Hz), 4.13–3.95(4H, m), 4.07(3H, s), 3.90(3H, s), 2.34(3H, s), 1.91–1.62(4H, m), 1.01(3H, t, J=7.6 Hz), 0.97(3H, t, J=7.6 Hz)

EXAMPLE 5

(E)-8-(4-Acetoxy-3-methoxystyryl)-1,3-diethyl-7-methylxanthine (Compound 5)

Substantially the same procedure as in Example 1 was repeated using 305 mg (0.823 mmol) of Compound f obtained in Reference Example 6. The obtained crude product was recrystallized from hexane/ethyl acetate to give 214 mg (63% yield) of Compound 5 as white crystals.

Melting Point:193.8°–194.6° C. Elemental Analysis:$C_{21}H_{24}N_4O_5$ Calcd. (%):C 61.16, H 5.86, N 13.58 Found (%):C 61.21, H 5.89, N 13.70 IR(KBr)vmax (cm$^{-1}$):1754, 1694, 1658, 1512, 1440. NMR (270 MHz; $CDCl_3$) δ(ppm):7.76(1H, d, J=15.8 Hz), 7.20(1H, dd, J=8.2, 2.0 Hz), 7.13(1H, d, J=2.0 Hz), 7.08(1H, d, J=8.2 Hz), 6.85(1H, d, J=15.8 Hz), 4.21(2H, q, J=6.9 Hz), 4.09(2H, q, J=6.9 Hz), 4.07(3H, s), 3.90(3H, s), 2.34(3H, s), 1.39(3H, t, J=6.9 Hz), 1.27(3H, t, J=6.9 Hz).

EXAMPLE 6

(E)-8-(4-Benzoyloxy-3-methoxystyryl)-7-methyl-1,3-dipropylxanthine (Compound 6)

Substantially the same procedure as in Example 2 was repeated using 200 mg (0.502 mmol) of Compound e obtained in Reference Example 5. The obtained crude product was recrystallized from hexane/ethyl acetate to give 219 mg (87% yield) of Compound 6 as pale yellow crystals.

Melting Point:156.1°–157.4° C. Elemental Analysis:$C_{28}H_{30}N_4O_5$ Calcd. (%):C 66.92, H 6.01, N 11.15 Found (%):C 66.87, H 5.84, N 11.11 IR(KBr)vmax (cm$^{-1}$):1731, 1693, 1649, 1540, 1509, 1437, 1251. NMR (270 MHz; $CDCl_3$) δ(ppm):8.24–8.21(2H, m), 7.78(1H, d, J=15.8 Hz), 7.68–7.50(3H, m), 7.27–7.18(3H, m), 6.88(1H, m), 4.14–3.96(4H, m), 4.08(3H, s), 3.89(3H, s), 1.89–1.66(4H, m), 1.01(3H, t, J=7.6 Hz), 0.97(3H, t, J=7.6 Hz).

EXAMPLE 7

(E)-8-(4-Benzoyloxy-3-methoxystyryl)-1,3-diethyl-7-methylxanthine (Compound 7)

Substantially the same procedure as in Example 2 was repeated using 200 mg (0.540 mmol) of Compound f obtained in Reference Example 6. The obtained crude product was recrystallized from hexane/ethyl acetate to give 170 mg (66% yield) of Compound 7 as yellow crystals.

Melting Point:234.3°–235.6° C. Elemental Analysis:$C_{26}H_{26}N_4O_5$ Calcd. (%):C 65.81, H 5.52, N 11.81 Found (%):C 65.52, H 5.58, N 11.79 IR(KBr) vmax (cm$^{-1}$):1735, 1694, 1652, 1540, 1509, 1436, 1253. NMR (270 MHz; $CDCl_3$) δ(ppm):8.24–8.21(2H, m), 7.79(1H, d, J=15.8 Hz), 7.68–7.50(3H, m), 7.28–7.19(3H, m), 6.88(1H, m), 4.22(2H, q, J=6.9 Hz), 4.10(2H, q, J=6.9 Hz), 4.08(3H, s), 3.89(3H, s), 1.39(3H, t, J=6.9 Hz), 1.27(3H, t, J=6.9 Hz).

EXAMPLE 8

(E)-8-(4-Benzoyloxystyryl)-1,3-diethyl-7-methylxanthine (Compound 8)

Substantially the same procedure as in Example 2 was repeated using 100 mg (0.294 mmol) of Compound g obtained in Reference Example 7. The obtained crude produck was recrystallized from ethyl acetate to give 108 mg (83% yield) of Compound 8 as yellow crystals.

Melting Point:208.4°–209.3° C. Elemental Analysis:$C_{25}H_{24}N_4O_4$ Calcd. (%):C 67.56, H 5.44, N 12.61 Found (%):C 67.46, H 5.40, N 12.53 IR(KBr) vmax (cm$^{-1}$):1693, 1655, 1510, 1265, 1215. NMR (270 MHz; $CDCl_3$) δ(ppm):8.22(2H, d, J=7.3 Hz), 7.81(1H, d, J=15.8 Hz), 7.67–7.50(5H, m), 7.29(2H, d, J=8.6 Hz), 6.90(1H, d, J=15.8 Hz), 4.32(2H, q, J=6.9 Hz), 4.10(2H, q, J=6.9 Hz), 4.07(3H, s), 1.39(3H, t, J=6.9 Hz), 1.27(3H, t, J=6.9 Hz).

EXAMPLE 9

(E)-8-(3,5-Diacetoxystyryl)-7-methyl-1,3-dipropylxanthine (Compound 9)

Substantially the same procedure as in Example 1 was repeated using 450 mg (1.171 mmol) of Compound h obtained in Reference Example 8. The obtained crude product was recrystallized from ethyl acetate to give 196 mg (36% yield) of Compound 9 as white crystals.

Melting Point:224.3°–225.1° C. Elemental Analysis:$C_{24}H_{28}N_4O_6$ Calcd. (%):C 61.53, H 6.02, N 11.96 Found (%):C 61.75, H 6.15, N 12.10 IR(KBr) vmax (cm$^{-1}$):1761, 1695, 1655, 1540, 1197. NMR (270 MHz; $CDCl_3$) δ(ppm):7.73(1H, d, J=15.8 Hz), 7.21(2H, d, J=2.0 Hz), 6.92(1H, t, J=2.0 Hz), 6.88(1H, d, J=15.8 Hz), 4.12–3.95 (4H, m), 4.06(3H, s), 2.32(6H, s), 1.89–1.62(4H, m), 1.00 (3H, t, J=7.6 Hz), 0.97(3H, t, J=7.6 Hz).

EXAMPLE 10

(E)-8-(4-Acetonyloxy-3-methoxystyryl)-1,3-diethyl-7-methylxanthine (Compound 10)

Compound f (200 mg, 0.540 mmol) obtained in Reference Example 6 was dissolved in 4 ml of dimethylformamide, and potassium carbonate (374 mg, 2.706 mmol) and bromoacetone (0.2 ml, 2.142 mmol) were added thereto, followed by stirring at room temperature for 7 hours. Water was added to the reaction mixture, and the resulting precipitate was collected by filtration. The obtained crude product was dissolved in chloroform, and the solution was washed with saturated aqueous sodium chloride three times, and dried over anhydrous sodium sulfate. The solvent was removed by evaporation, and the residue was recrystallized from ethyl acetate to give 172 mg (75% yield) of Compound 10 as pale yellow crystals.

Melting Point:205.7°–206.1° C. Elemental Analysis:$C_{22}H_{26}N_4 O_5$ Calcd. (%):C 61.96, H 6.14, N 13.14 Found (%):C 61.97, H 6.30, N 12.98 IR(KBr) vmax ($c^{-1}$):1694, 1660, 1515, 1262. NMR (270 MHz; $CDCl_3$) δ(ppm):7.73(1H, d, J=15.8 Hz), 7.23–7.12(2H, m), 6.78(1H, d, J=15.8 Hz), 6.77(1H, d, J=8.6 Hz), 4.64(2H, s), 4.21(2H, q, J=6.9 Hz), 4.09(2H, q, J=6.9 Hz), 4.07(3H, s), 3.96(3H, s), 2.30(3H, s), 1.38(3H, t, J=6.9 Hz), 1.27(3H, t, J=6.9 Hz).

EXAMPLE 11

(E)-1,3-Diethyl-8-(3-methoxy-4-phenacyloxystyryl)-7-methylxanthine (Compound 11)

Compound f (200 mg, 0.540 mmol) obtained in Reference Example 6 was dissolved in 4 ml of dimethylformamide, and potassium carbonate (149 mg, 1.078 mmol) and bromoacetophenone (161 mg, 0.809 mmol) were added thereto, followed by stirring at room temperature overnight. Water was added to the reaction mixture, and the resulting precipitate was collected by filtration. The obtained crude product was dissolved in chloroform, and the solution was washed with saturated aqueous sodium chloride three times, and dried over anhydrous sodium sulfate. The solvent was removed by evaporation, and the residue was recrystallized from ethyl acetate to give 177 mg (67% yield) of Compound 11 as pale yellow crystals.

Melting Point:180.4°–182.1° C. Elemental Analysis:$C_{27}H_{28}N_4 O_5$ Calcd. (%):C 66.38, H 5.77, N 11.47 Found (%):C 66.18, H 5.81, N 11.37 IR(KBr) vmax (cm⁻¹):1688, 1656, 1516, 1256. NMR (270 MHz; $CDCl_3$) δ(ppm):8.03–8.00(2H, m), 7.72(1H, d, J=15.8 Hz), 7.66–7.48(3H, m), 7.12–7.10(2H, m), 6.84–6.81(1H, m), 6.76(1H, d, J=15.8 Hz), 5.41(2H, s), 4.21(2H, q, J=6.9 Hz), 4.09(2H, q, J=6.9 Hz), 4.05(3H, s), 3.96(3H, s), 1.38(3H, t, J=6.9 Hz), 1.26(3H, t, J=6.9 Hz).

EXAMPLE 12

(E)-1,3-Diethyl-8-(3-methoxy-4-propionyloxystyryl)-7-methylxanthine (Compound 12)

Substantially the same procedure as in Example 1 was repeated using 1.00 g (2.70 mmol) of Compound f obtained in Reference Example 6, and 0.69 ml (5.38 mmol) of propionic anhydride in place of acetic anhydride. The obtained crude product was recrystallized from ethyl acetate to give 815 mg (71% yield) of Compound 12 as yellow crystals.

Melting Point:183.6°–183.9° C. Elemental Analysis:$C_{22}H_{26}N_4 O_5$ Calcd. (%):C 61.96, H 6.14, N 13.14 Found (%):C 61.86, H 6.15, N 13.10 IR(KBr) vmax (cm⁻¹):1764, 1691, 1654, 1542, 1510, 1435. NMR (270 MHz; $CDCl_3$) δ(ppm):7.76(1H, d, J=15.5 Hz), 7.20(1H, d, J=7.9 Hz), 7.13(1H, s), 7.07(1H, d, J=7.9 Hz), 6.85(1H, d, J=15.5 Hz), 4.21(2H, q, J=6.9 Hz), 4.09(2H, q, J=6.9 Hz), 4.07(3H, s), 3.89(3H, s), 2.64(2H, q, J=7.6 Hz), 1.39(3H, t, J=6.9 Hz), 1.29(3H, t, J=7.6 Hz), 1.27(3H, t, J=6.9 Hz).

EXAMPLE 13

(E)-1,3-Diethyl-8-(3-methoxy-4-pivaloyloxystyryl)-7-methylxanthine (Compound 13)

Substantially the same procedure as in Example 2 was repeated using 1.00 g (2.70 mmol) of Compound f obtained in Reference Example 6, and 0.67 ml (5.44 mmol) of pivaloyl chloride in place of benzoyl chloride. The obtained crude product was recrystallized from ethyl acetate to give 722 mg (59% yield) of Compound 13 as pale yellow crystals.

Melting Point:207.7°–208.3° C. Elemental Analysis:$C_{24}H_{30}N_4 O_5$ Calcd. (%):C 63.42, H 6.65, N 12.33 Found (%):C 63.44, H 6.66, N 12.31 IR(KBr) vmax (cm⁻¹):1756, 1694, 1658, 1437, 1108. NMR (270 MHz; $CDCl_3$) δ(ppm):7.76(1H, d, J=15.5 Hz), 7.20(1H, dd, J=7.9, 1.7 Hz), 7.12(1H, d, J=1.7 Hz), 7.04(1H, d, J=7.9 Hz), 6.85(1H, d, J=15.5 Hz), 4.21(2H, q, J=6.9 Hz), 4.09(2H, q, J=6.9 Hz), 4.07(3H, s), 3.88(3H, s), 1.39(3H, t, J=6.9 Hz), 1.38(9H, s), 1.27(3H, t, J=6.9 Hz).

EXAMPLE 14

(E)-8-(4-Acetoxystyryl)-1,3-diethyl-7-methylxanthine (Compound 14)

Substantially the same procedure as in Example 1 was repeated using 600 mg (1.76 mmol) of Compound g obtained in Reference Example 7. The obtained crude product was recrystallized from ethyl acetate to give 399 mg (59% yield) of Compound 14 as white crystals.

Melting Point:197.7°–198.1° C. Elemental Analysis:$C_{20}H_{22}N_4 O_4$ Calcd. (%):C 62.82, H 5.80,N 14.65 Found (%):C 62.69, H 5.77,N 14.65 IR(KBr) vmax (cm⁻¹):1760, 1694, 1659, 1543, 1223. NMR (270 MHz; $CDCl_3$) δ(ppm):7.78(1H, d, J=15.8 Hz), 7.60(2H, d, J=8.6 Hz), 7.15(2H, d, J=8.6 Hz), 6.87(1H, d, J=15.8 Hz), 4.22(2H, q, J=6.9 Hz), 4.09(2H, q, J=6.9 Hz), 4.06(3H, s), 2.33(3H, s), 1.39(3H, t, J=6.9 Hz), 1.27(3H, t, J=6.9 Hz).

EXAMPLE 15

(E)-8-(4-Acetoxy-3-methoxystyryl)-1,3-diallyl-7-methylxanthine (Compound 15)

Substantially the same procedure as in Example 1 was repeated using 800 mg (2.03 mmol) of Compound i obtained in Reference Example 9. The obtained crude product was recrystallized from toluene to give 830 mg (94% yield) of Compound 15 as white crystals.

Melting Point:207.0°–208.0° C. Elemental Analysis:$C_{23}H_{24}N_4 O_5$ Calcd. (%):C 63.29, H 5.54,N 12.84 Found (%):C 63.53, H 5.31,N 12.51 IR(KBr) vmax (cm⁻¹):1752, 1657, 1644, 1511, 1203. NMR (270 MHz; DMSO-d6) δ(ppm):7.66(1H, d, J=15.8 Hz), 7.56(1H, s), 7.40(1H, d, J=8.3 Hz), 7.37(1H, d, J=15.8 Hz), 7.14(1H, d, J=8.3 Hz), 5.98–5.82(2H, m), 5.18–5.04(4H, m), 4.64(2H, d, J=5.3 Hz), 4.49(2H, d, J=5.3 Hz), 4.06(3H, s), 3.86(3H, s), 2.27(3H, s).

EXAMPLE 16

(E)-8-(3-Acetoxy-4-methoxystyryl)-1,3-diethyl-7-methylxanthine (Compound 16)

Substantially the same procedure as in Example 1 was repeated using 1.00 g (2.70 mmol) of Compound j obtained in Reference Example 10. The obtained crude product was recrystallized from ethyl acetate to give 807 mg (72% yield) of Compound 16 as pale yellow crystals.

Melting Point:241.3°–241.9° C. Elemental Analysis:$C_{21}H_{24}N_4O_5$ Calcd. (%):C 61.16, H 5.86,N 13.58 Found (%):C 61.08, H 6.07,N 13.80 IR(KBr) vmax (cm$^{-1}$) :1759, 1694, 1659, 1543, 1515, 1440, 1273, 1220. NMR (270 MHz; CDCl$_3$) δ(ppm):7.71(1H, d, J=15.8 Hz), 7.40 (1H, dd, J=8.6, 2.3 Hz), 7.32(1H, d, J=2.3 Hz), 6.99(1H, d, J=8.6 Hz), 6.75(1H, d, J=15.8 Hz), 4.21(2H, q, J=6.9 Hz), 4.09(2H, q, J=6.9 Hz), 4.04(3H, s), 3.88(3H, s), 2.35(3H, s), 1.38(3H, t, J=6.9 Hz), 1.26(3H, t, J=6.9 Hz).

EXAMPLE 17

(E)-8-(4-Acetoxy-3,5-dimethoxystyryl)-1, 3-diethyl-7-methylxanthine (Compound 17)

Substantially the same procedure as in Example 1 was repeated using 1.50 g (3.75 mmol) of Compound k obtained in Reference Example 11. The obtained crude product was recrystallized from ethanol/N, N-dimethylformamide to give 1.13 g (68% yield) of Compound 17 as yellow powders.

Melting Point:248.4°–248.9° C. Elemental Analysis:$C_{22}H_{26}N_4O_6$ Calcd. (%):C 59.72, H 5.92,N 12.66 Found (%):C 59.85, H 6.22,N 12.64 IR(KBr) vmax (cm$^{-1}$) :1689, 1659, 1597, 1340, 1190, 1129. NMR (270 MHz; CDCl$_3$) δ(ppm):7.73(1H, d, J=15.8 Hz), 6.83(1H, d, J=15.8 Hz), 6.81(2H, s), 4.21(2H, q, J=6.9 Hz), 4.09(2H, q, J=6.9 Hz), 4.08(3H, s), 3.89(6H, s), 2.36(3H, s), 1.39(3H, t, J=6.9 Hz), 1.27(3H, t, J=6.9 Hz).

EXAMPLE 18

(E)-8-(4-Benzoyloxy-3,5-dimethoxystyryl)-1,3-diethyl-7-methylxanthine (Compound 18)

Substantially the same procedure as in Example 2 was repeated using 1.50 g (3.75 mmol) of Compound k obtained in Reference Example 11. The obtained crude product was recrystallized from toluene/cyclohexane to give 1.16 g (61% yield) of Compound 18 as pale yellow crystals.

Melting Point:195.7°–196.320 C. Elemental Analysis:$C_{27}H_{28}N_4O_6$ Calcd. (%):C 64.28, H 5.59,N 11.10 Found (%):C 64.16, H 5.61,N 11.03 IR(KBr) vmax (cm$^{-1}$) :1740, 1699, 1658, 1653, 1508, 1342. NMR (270 MHz; CDCl$_3$) δ(ppm):8.24(2H, dd, J=7.9, 1.7 Hz), 7.76(1H, d, J=15.8 Hz), 7.65(1H, dt, J=7.9, 1.7 Hz), 7.52(2H, t, J=7.9 Hz), 6.87(1H, d, J=15.8 Hz), 6.86(2H, m), 4.22(2H, q, J=6.9 Hz), 4.10(2H, q, J=6.9 Hz), 4.09(3H, s), 3.87(6H, s), 1.40 (3H, t, J=6.9 Hz), 1.27(3H, t, J=6.9 Hz).

EXAMPLE 19

(E)-8-(4-Acetoxy-3,5-dimethoxystyryl)-1,3-diallyl-7-methylxanthine (Compound 19)

Substantially the same procedure as in Example 1 was repeated using 1.19 g (2.81 mmol) of Compound m obtained in Reference Example 12. The obtained crude product was recrystallized from ethanol/N, N-dimethylformamide to give 680 mg (52% yield) of Compound 19 as white powders.

Melting Point:220.5°–221.1° C. Elemental Analysis:$C_{24}H_{26}N_4O_6$ Calcd. (%):C 61.79, H 5.62,N 12.01 Found (%):C 61.74, H 5.78,N 12.07 IR (KBr) vmax (cm$^{-1}$):1762, 1708, 1671, 1610, 1137. NMR (270 MHz; CDCl$_3$) δ(ppm):7.73(1H, d, J=15.8 Hz), 6.82(1H, d, J=15.8 Hz), 6.81(2H, s), 6.11–5.87(2H, m), 5.35–5.17(4H, m), 4.76(2H, d, J=5.4 Hz), 4.65(2H, d, J=5.4 Hz), 4.08(3H, s), 3.89(6H, s), 2.36(3H, s).

EXAMPLE 20

(E)-1,3-Diallyl-8-(4-benzoyloxy-3,5-dimethoxystyryl)-7-methylxanthine (Compound 20)

Substantially the same procedure as in Example 2 was repeated using 1.00 g (2.36 mmol) of Compound m obtained in Reference Example 12. The obtained crude product was recrystallized from toluene/cyclohexane to give 990 mg (79% yield) of Compound 20 as white powders.

Melting Point:178.6°–179.8° C. Elemental Analysis:$C_{29}H_{28}N_4O_6$ Calcd. (%):C 65.90, H 5.34,N 10.60 Found (%):C 66.00, H 5.40,N 10.58 IR(KBr) vmax (cm$^{-1}$) :1737, 1699, 1665, 1593, 1434, 1341, 1267, 1254. NMR (270 MHz; CDCl$_3$) δ(ppm):8.23(2H, dd, J=7.4, 1.5 Hz), 7.77(1H, d, J=15.8 Hz), 7.65(1H, dt, J=7.4, 1.5 Hz), 7.52 (2H, t, J=7.4 Hz), 6.86(1H, d, J=15.8 Hz), 6.85(2H, s), 6.11–5.88(2H, m), 5.36–5.18(4H, m), 4.77(2H, d, J=5.4 Hz), 4.65(2H, d, J=5.4 Hz), 4.09(3H, s), 3.87(6H, s).

EXAMPLE 21

(E)-8-(3-Acetoxystyryl)-1,3-diethyl-7-methylxanthine (Compound 21)

Substantially the same procedure as in Example 1 was repeated using 3.00 g (8.81 mmol) of Compound n obtained in Reference Example 13. The obtained crude product was recrystallized from ethyl acetate to give 2.80 g (86% yield) of Compound 21 as white crystals.

Melting Point:206°–207° C. Elemental Analysis:$C_{20}H_{22}N_4O_4$ Calcd. (%):C 62.80, H 5.80,N 14.65 Found (%):C 62.83, H 6.03,N 14.56 IR(KBr) vmax (cm$^{-1}$) :1781, 1711, 1683, 1565, 1516, 1466. NMR (270 MHz; DMSO-d$_6$) δ(ppm):7.65(1H, d, J=15.8 Hz), 7.65(1H, s), 7.63(1H, d, J=8.3 Hz), 7.45(1H, t, J=8.3 Hz), 7.39(1H, d, J=15.8 Hz), 7.13(1H, d, J=8.3 Hz),4.07(2H, q, J=6.9 Hz), 4.04(3H, s, 3.92(2H, q, J=6.9 Hz), 2.30(3H, s) 1.26(3H, t, J=6.9 Hz), 1.13(3H, t, J=6.9 Hz).

EXAMPLE 22

(E)-8-(3-Benzoyloxystyryl)-1,3-diethyl-7-methylxanthine (Compound 22)

Substantially the same procedure as in Example 2 was repeated using 800 mg (2.23 mmol) of Compound n obtained in Reference Example 13. The obtained crude product was recrystallized from toluene/hexane to give 962 mg (97% yield) of Compound 22 as white powders.

Melting Point:223°–224° C. Elemental Analysis:$C_{25}H_{24}N_4O_4$ Calcd. (%):C 67.55, H 5.44,N 12.61 Found (%):C 67.63, H 5.68,N 12.43 IR(KBr) vmax (cm$^{-1}$) :1748, 1606, 1516, 1456, 1422. NMR (270 MHz; CDCl$_3$) δ(ppm):8.21(2H, dd, J=8.3, 1.5 Hz), 7.81(1H, d, J=15.3 Hz), 7.67(1H, t, J=7.4 Hz), 7.46–7.57(5H, m), 7.20–7.24(1H, m), 6.93(1H, d, J=15.3 Hz), 4.21(2H, q, J=6.9 Hz), 4.08(2H, q, J=6.9 Hz), 4.06(3H, s), 1.38(3H, t, J=6.9 Hz), 1.26(3H, t, J=6.9 Hz).

EXAMPLE 23

(E)-8-(2-Acetoxy-5-methoxystyryl)-1,3-diethyl-7-methylxanthine (Compound 23)

Substantially the same procedure as in Example 1 was repeated using 3.00 g (8.10 mmol) of Compound o obtained in Reference Example 14. The obtained crude product was recrystallized from ethyl acetate to give 3.25 g (97% yield) of Compound 23 as yellow crystals.

Melting Point:186°–187° C. Elemental Analysis:$C_{21}H_{24}N_4O_5$ Calcd. (%):C 61.15, H 5.87,N 13.59 Found (%):C 61.24, H 6.21,N 13.75 IR(KBr) vmax (cm$^{-1}$) :1767, 1672, 1613, 1492, 1454, 1426. NMR (270 MHz; DMSO-$d_6$) δ(ppm):7.76(1H, d, J=15.8 Hz), 7.15(1H, d, J=3.0 Hz), 7.05(1H, d, J=8.9 Hz), 6.92(1H, dd, J=3.0, 8.9 Hz), 6.89(1H, d, J=15.8 Hz), 4.20(2H, q, J=6.9 Hz), 4.09 (2H, q, J=6.9 Hz), 4.04(3H, s), 3.86(3H, s), 2.37(3H, s), 1.37(3H, t, J=6.9 Hz), 1.26(3H, t, J=6.9 Hz).

EXAMPLE 24

(E)-8-(2-Benzoyloxy-5-methoxystyryl)-1,3-diethyl-7-methylxanthine (Compound 24)

Substantially the same procedure as in Example 2 was repeated using 800 mg (2.16 mmol) of Compound o obtained in Reference Example 14. The obtained crude product was recrystallized from N,N-dimethylformamide/water to give 972 mg (95% yield) of Compound 24 as yellow powders.

Melting Point:254°–255° C. Elemental Analysis:$C_{26}H_{26}N_4O_5$ Calcd. (%):C 65.81, H 5.52,N 11.81 Found (%):C 65.81, H 5.74,N 11.73 IR(KBr) vmax (cm$^{-1}$) :1744, 1614, 1559, 1521, 1425. NMR (270 MHz; CDCl$_3$) δ(ppm):8.27(2H, dd, J=7.6, 1.3 Hz), 7.81(1H, d, J=15.8 Hz), 7.68(1H, dt, J=1.3, 7.6 Hz), 7.54(2H, t, J=7.6 Hz), 7.21(1H, d, J=8.9 Hz), 7.18(1H, d, J=3.3 Hz), 6.96(1H, dd, J=3.3, 8.9 Hz), 6.93(1H, d, J=15.8 Hz), 4.10(2H, q, J=6.9 Hz), 4.05 (2H, q, J=6.9 Hz), 3.88(3H, s), 3.83(3H, s), 1.24(3H, t, J=6.9 Hz), 1.23(3H, t, J=6.9 Hz).

EXAMPLE 25

(E)-8-(2-Acetoxy-3-methoxystyryl)-1,3-diethyl-7-methylxanthine (Compound 25)

Substantially the same procedure as in Example 1 was repeated using 2.00 g (5.40 mmol) of Compound p obtained in Reference Example 15. The obtained crude product was recrystallized from ethyl acetate to give 2.01 g (90% yield) of Compound 25 as white crystals.

Melting Point:201.5°–202.8° C. Elemental Analysis:$C_{21}H_{24}N_4O_5$ Calcd. (%):C 61.16, H 5.86,N 13.58 Found (%):C 61.04, H 6.09,N 13.45 IR(KBr) vmax (cm$^{-1}$) :1765, 1695, 1657, 1544, 1444, 1280. NMR (270 MHz; CDCl$_3$) δ(ppm):7.80(1H, d, J=15.8 Hz), 7.30–7.21(2H, m), 6.98(1H, dd, J=6.9, 2.3 Hz), 6.93(1H, d, J=15.8 Hz), 4.21 (2H, q, J=6.9 Hz), 4.09(2H, q, J=6.9 Hz), 4.04(3H, s), 3.86(3H, s), 2.41(3H, s), 1.38(3H, t, J=6.9 Hz), 1.26(3H, t, J=6.9 Hz).

EXAMPLE 26

(E)-8-(2,3-Diacetoxystyryl)-1,3-diethyl-7-methylxanthine (Compound 26)

Substantially the same procedure as in Example 1 was repeated using 685 mg (1.92 mmol) of Compound q obtained in Reference Example 16. The obtained crude product was recrystallized from ethyl acetate to give 601 mg (71% yield) of Compound 26 as pale brown crystals.

Melting Point:228.3°–230.2° C. Elemental Analysis:$C_{22}H_{24}N_4O_6$ Calcd. (%):C 59.99, H 5.49,N 12.72 Found (%):C 59.86, H 5.72,N 12.73 IR(KBr) vmax (cm$^{-1}$) :1769, 1692, 1665, 1220. NMR (270 MHz; CDCl$_3$) δ(ppm) :7.77(1H, d, j=15.8 Hz), 7.57(1H, dd, J=7.9, 1.7 Hz), 7.31 (1H, t, J=7.9 Hz), 7.22(1H, dd, J=7.9, 1.7 Hz), 6.93(1H, d, J=15.8 Hz), 4.20(2H, q, J=6.9 Hz), 4.09(2H, q, J=6.9 Hz), 4.05(3H, s), 2.39(3H, s), 2.31(3H, s), 1.37(3H, t, J=6.9 Hz), 1.26(3H, t, J=6.9 Hz).

EXAMPLE 27

(E)-8-(3-Acetoxy-4,5-methylenedioxystyryl)-1,3-diethyl-7-methylxanthine (Compound 27)

Substantially the same procedure as in Example 1 was repeated using 2.00 g (5.02 mmol) of Compound r obtained in Reference Example 17. The obtained crude product was purified by silica gel column chromatography to give 471 mg (22% yield) of Compound 27 as a yellow solid, which was recrystallized from dioxane/water to give yellow powders.

Melting Point:>270° C. Elemental Analysis:$C_{21}H_{22}N_4O_6$ Calcd. (%):C 59.15, H 5.20,N 13.14 Found (%):C 59.13, H 5.31,N 13.07 IR(KBr) vmax (cm$^{-1}$):1709, 1673, 1520, 1460, 1309. NMR (270 MHz; CDCl$_3$) δ(ppm):7.66(1H, d, J=15.8 Hz), 6.98(1H, d, J=1.7 Hz), 6.88(1H, d, J=1.7 Hz), 6.73(1H, d, J=15.8 Hz), 6.06(2H, s), 4.20(2H, q, J=6.9 Hz), 4.09(2H, q, J=6.9 Hz), 4.04(3H, s), 2.34(3H, s), 1.37(3H, t, J=6.9 Hz), 1.26(3H, t, J=6.9 Hz).

REFERENCE EXAMPLE 1

(E)-8-(3,4-Dihydroxystyryl)-7-methyl-1,3-dipropylxanthine (Compound a)

Boron tribromide (5.6 ml, 5.6 mmol) in 1.0M methylene chloride solution was added to an ice-cooled solution of 770 mg (1.87 mmol) of (E)-8-(3, 4-dimethoxystyryl)-7-methyl-1, 3-dipropylxanthine (WO92/06976) in 15 ml of methylene chloride in an atmosphere of argon, followed by stirring at room temperature overnight. Methanol was added to the reaction mixture, followed by partitioning between chloroform and sodium hydrogen carbonate solution. The organic layer was washed with saturated aqueous sodium chloride, and dried over anhydrous sodium sulfate. The solvent was removed by evaporation, and the residue was purified by silica gel column chromatography to give 550 mg (77% yield) of Compound a as a yellow solid, which was micropowdered by ether to give yellow powders.

Melting Point:250.1°–251.4° C. Elemental Analysis:$C_{20}H_{24}N_4O_4$ Calcd. (%):C 62.49, H 6.29, N 14.57 Found (%):C 62.27, H 6.48, N 14.74 IR(KBr) vmax (cm$^{-1}$):1680, 1640, 1543, 1306. NMR (270 MHz; DMSO-$d_6$) δ(ppm):9.31(1H, brs), 8.95(1H, brs), 7.49(1H, d, J=15.8 Hz), 7.15(1H, d, J=2.0 Hz), 7.04(1H, dd, J=7.9, 2.0 Hz), 6.98(1H, d, J=15.8 Hz), 6.78(1H, d, J=7.9 Hz), 3.99(2H, t, J=7.6 Hz), 3.98(3H, s), 3.84(2H, t, J=7.4 Hz), 1.73(2H, m), 1.57(2H, m), 0.90(3H, t, J=7.4 Hz), 0.87(3H, t, J=7.4 Hz).

RFERENCE EXAMPLE 2

(E)-8-(3-Hydroxy-4-methoxystyryl)-7-methyl-1,3-dipropylxanthine (Compound b)

Compound a (500 mg, 1.30 mmol) obtained in Reference Example 1 was dissolved in 10 ml of dimethylformamide, and methyl iodide (0.40 ml, 6.43 mmol) and lithium carbonate (400 mg, 6.50 mmol) were added thereto, followed by heating at 80° C. for 5 hours. Water was added to the reaction mixture to dissolve lithium carbonate, and the resulting precipitate was collected by filtration. The obtained crude product was dissolved in chloroform, and the solution was washed with saturated aqueous sodium chloride. The solvent was removed by evaporation, and the residue was purified by silica gel column chromatography, and subsequently recrystallized from hexane/ethyl acetate to give 162 mg (31% yield) of Compound b as yellow crystals.

Melting Point:200.3°–203.6° C. EI-MS (m/z):398(M$^+$) IR(KBr) vmax (cm$^{-1}$):1683, 1642, 1512, 1278. NMR (270 MHz; DMSO-d$_6$) δ(ppm):8.98(1H, brs), 7.52(1H, d, J=15.5 Hz), 7.22(1H, d, J=2.0 Hz), 7.15(1H, dd, J=8.3, 2.0 Hz), 7.06(1H, d, J=15.5 Hz), 6.96(1H, d, J=8.3 Hz), 4.02–3.97 (2H, m), 4.00(3H, s), 3.84–3.82(2H, m), 3.82(3H, s), 1.80–1.50(4H, m), 0.90(3H, t, J=7.3 Hz), 0.87(3H, t, J=7.3 Hz).

REFERENCE EXAMPLE 3

(E)-8-(3-Methoxy-4-methoxymethoxystyryl)-1,3-dipropylxanthine (Compound c)

3-Methoxy-4-methoxymethoxy cinnamic acid (4.63 g, 19.4 mmol) and 3-(3-diethylaminopropyl)-1-ethylcarbodiimido hydrochloride (5.08 g) were added to a mixed solution of 4.00 g (17.7 mmol) of 5,6-diamino-1,3-dipropyluracil [J. Med. Chem., 28, 487 (1985)] in 50 ml of dioxane/25 ml of water. The solution was stirred at room temperature for 1 hour while adjusting to pH 5.5. The reaction mixture was cooled to room temperature, then 1.59 g of sodium hydroxide and 2N sodium hydroxide solution (50 ml) were added thereto. The mixture was heated under reflux for 1 hour, followed by cooling. The mixture was neutralized by adding 2N hydrochloric acid and the resulting precipitate was collected by filtration. The obtained crude product was recrystallized from dioxane/water to give 5.06 g (67% yield) of Compound c as pale yellow crystals.

Melting Point:226.7°–227.4° C. Elemental Analysis:C$_{22}$H$_{28}$N$_4$O$_5$ Calcd. (%):C 61.67, H 6.58, N 13.08 Found (%):C 61.56, H 6.68, N 13.09 IR(KBr) vmax (cm$^{-1}$):1697, 1655, 1650, 1516, 1255. NMR (270 MHz; DMSO-d$_6$) δ(ppm):13.47(1H, brs), 7.60(1H, d, J=16.5 Hz), 7.31(1H, s), 7.10(2H, m), 7.00(1H, d, J=16.5 Hz), 5.19(2H, s), 3.98 (2H, t, J=6.9 Hz), 3.88–3.83(5H, m), 3.40(3H, s), 1.79–1.66 (2H, m), 1.62–1.51(2H, m), 0.90(3H, t, J=7.6 Hz), 0.88(3H, t, J=7.6 Hz).

REFERENCE EXAMPLE 4

(E)-8-(3-Methoxy-4-methoxymethoxystyryl)-7-methyl-1,3-dipropylxanthine (Compound d)

Compound c (4.5 g, 10.5 mmol) obtained in Reference Example 3 was dissolved in 90 ml of dimethylformamide, and potassium carbonate (3.63 g, 26.26 mmol) and methyl iodide (1.31 ml, 21.04 mmol) were added thereto, followed by stirring at 50° C. for 1 hour. After cooling, water was added to the reaction mixture, and the resulting precipitate was collected by filtration. The obtained crude product was recrystallized from hexane/ethyl acetate to give 3.66 g (79% yield) of Compound d as pale yellow crystals.

Mealting Point:153.2°–154.9° C. Elemental Analysis:C$_{23}$H$_{30}$N$_4$O$_5$ Calcd. (%):C 62.43, H 6.83, N 12.66 Found (%):C 62.42, H 6.95, N 13.05 IR(KBr) vmax (cm$^{-1}$):1697, 1656, 1544, 1254. NMR (270 MHz; CDCl$_3$) δ(ppm):7.73(1H, d, J=15.8 Hz), 7.20–7.13(2H, m), 7.10(1H, m), 6.78(1H, d, J=15.8 Hz), 5.28(2H, s), 4.14–4.08(2H, m), 4.06(3H, s), 4.01–3.97(2H, m), 3.96(3H, s), 3.53(3H, s), 1.91–1.77(2H, m), 1.76–1.63(2H, m), 1.01(3H, t, J=7.6 Hz), 0.97(3H, t, J=7.6 Hz).

REFERENCE EXAMPLE 5

(E)-8-(4-Hydroxy-3-methoxystyryl)-7-methyl-1,3-dipropylxanthine (Compound e)

Compound d (3.00 g, 6.78 mmol) obtained in Reference Example 4 was suspended in 60 ml of tetrahydrofuran, and 2N hydrochloric acid (17 ml) was added thereto, followed by heating under reflux for 1 hour. The reaction mixture was neutralized by adding 2N sodium hydroxide under ice-cooling. Water was added to the reaction mixture, and the resulting precipitate was collected by filtration. The obtained crude product was recrystallized from hexane/ethyl acetate to give 1.93 g (72% yield) of Compound e as pale yellow crystals.

Melting Point:186.8°–187.9° C. Elemental Analysis:C$_{21}$H$_{26}$N$_4$O$_4$ Calcd. (%):C 63.30, H 6.57, N 14.06 Found (%):C 63.19, H 6.69, N 14.25 IR(KBr) vmax (cm$^{-1}$):1693, 1650, 1540, 1520, 1284. NMR (270 MHz; DMSO-d$_6$) δ(ppm):9.44(1H, brs), 7.57(1H, d, J=15.5 Hz), 7.39(1H, s), 7.19(1H, d, J=8.3 Hz), 7.13(1H, d, J=15.5 Hz), 6.81(1H, d, J=8.3 Hz), 4.01(3H, s), 3.99(2H, t, J=7.6 Hz), 3.86(3H, s), 3.84(2H, t, J=7.6 Hz), 1.77–1.66(2H, m), 1.63–1.50(2H, m), 0.90(3H, t, J=7.6 Hz), 0.87(3H, t, J=7.6 Hz).

Compounds of the following Reference Examples 6 to 16 were obtained from the corresponding uracil derivatives and cinnamic acid derivatives according to the procedures of Reference Examples 3 to 5.

REFERENCE EXAMPLE 6

(E)-1,3-Diethyl-8-(4-hydroxy-3-methoxystyryl)-7-methylxanthine Compound f)

Melting Point:185.3°–186.5° C. (ethyl acetate) Elemental Analysis:C$_{19}$H$_{22}$N$_4$O$_4$.H$_2$O Calcd. (%):C 58.75, H 6.23, N 14.42 Found (%):C 59.13, H 6.21, N 14.39 IR(KBr) vmax (cm$^{-1}$):1687, 1657, 1650, 1515, 1276. NMR (270 MHz; DMSO-d$_6$) δ(ppm):9.45(1H, brs), 7.59(1H, d, J=15.8 Hz), 7.39(1H, d, J=2.0 Hz), 7.19(1H, dd, J=7.9, 2.0 Hz), 7.14(1H, d, J=15.8 Hz), 6.81(1H, d, J=7.9 Hz), 4.06(2H, q, J=6.9 Hz), 4.02(3H, s), 3.91(2H, q, J=6.9 Hz), 3.86(3H, s), 1.26(3H, t, J=6.9 Hz), 1.13(3H, t, J=6.9 Hz).

REFERENCE EXAMPLE 7

(E)-1,3-Diethyl-8-(4-hydroxystyryl)-7-methylxanthine (Compound g)

Melting Point:>270° C. (isopropanol) Elemental Analysis:C$_{18}$H$_{20}$N$_4$O$_3$ Calcd. (%):C 63.52, H 5.92, N 16.46 Found (%):C 63.17, H 6.02, N 16.18 IR(KBr) vmax (cm$^{-1}$):1696, 1636, 1607, 1517. NMR (270 MHz; DMSO-d$_6$) δ(ppm):9.79(1H, s), 7.62(2H, d, J=8.3 Hz), 7.58(1H, d, J=15.8 Hz), 7.08(1H, d, J=15.8 Hz), 6.81(2H, d, J=8.3 Hz), 4.07(2H, q, J=6.9 Hz), 3.99(3H, s), 3.92(2H, q, J=6.9 Hz), 1.26(3H, t, J=6.9 Hz), 1.13(3H, t, J=6.9 Hz).

REFERENCE EXAMPLE 8

(E)-1,3-Dipropyl-8-(3,5-dihydroxystyryl)-7-methylxanthine (Compound h)

EI-MS (m/z):384(M$^+$) NMR (270 MHz; DMSO-d$_6$) δ(ppm):9.37(2H, s), 7.45(1H, d, J=15.8 Hz), 7.13(1H, d, J=15.8 Hz), 6.59(2H, s), 6.28(1H, s), 4.01(3H, s), 4.10–3.81 (4H, m), 1.76–1.53(4H, m), 0.93–0.84(6H, m).

REFERENCE EXAMPLE 9

(E)-1,3-Diallyl-8-(4-hydroxy-3-methoxystyryl)-7-methylxanthine (Compound i)

Melting Point:202.0°–203.0° C. (toluene/cyclohexane) Elemental Analysis:C$_{21}$H$_{22}$N$_4$O$_4$ Calcd. (%):C 63.95, H 5.62,N 14.20 Found (%):C 64.05, H 5.80,N 13.98 IR(KBr) vmax (cm⁻¹):1688, 1639, 1523, 1283. NMR (270 MHz; DMSO-d₆) δ(ppm):9.47(1H, brs), 7.57(1H, d, J=15.5 Hz), 7.39(1H, s), 7.19(1H, d, J=7.3 Hz), 7.14(1H, d, J=15.5 Hz), 6.81(1H, d, J=7.9 Hz), 6.03–5.79(2H, m), 5.21–5.03(4H, m), 4.63(2H, d, J=4.6 Hz), 4.48(2H, d, J=4.6 Hz), 4.02(3H, s), 3.86(3H, s).

REFERENCE EXAMPLE 10

(E)-1,3-Diethyl-8-(3-hydroxy-4-methoxystyryl)-7-methylxanthine (Compound j)

Melting Point:204.5°–205.8° C. (ethyl acetate) Elemental Analysis:$C_{19}H_{22}N_4 O_4$ Calcd. (%):C 61.61, H 5.98,N 15.13 Found (%):C 61.49, H 6.06,N 14.98 IR(KBr) vmax (cm⁻¹):1689, 1653, 1515, 1442. NMR (270 MHz; DMSO-d₆) δ(ppm):9.06(1H,brs), 7.53(1H, d, J=15.5 Hz), 7.23(1H, s), 7.17(1H, d, J=8.3 Hz), 7.08(1H, d, J=15.5 Hz), 6.96(1H, d, J=8.3 Hz), 4.06(2H, q, J=6.9 Hz), 4.00(3H, s), 3.92(2H, q, J=6.9 Hz), 3.82(3H, s), 1.25(3H, t, J=6.9 Hz), 1.13(3H, t, J=6.9 Hz).

REFERENCE EXAMPLE 11

(E)-1,3-Diethyl-8-(4-hydroxy-3,5-dimethoxystyryl)-7-methylxanthine (Compound k)

Melting Point:225.9°–226.4° C. (toluene/cyclohexane) Elemental Analysis:$C_{20}H_{24}N_4 O_5$ Calcd. (%):C 59.99, H 6.04,N 13.99 Found (%):C 59.89, H 6.08,N 13.94 IR(KBr) vmax (cm⁻¹):1689, 1656, 1641, 1514, 1334. NMR (270 MHz; CDCl₃) δ(ppm):7.71(1H, d, J=15.8 Hz), 6.82(2H, s), 6.75(1H, d, J=15.8 Hz), 5.75(1H, brs), 4.21(2H, q, J=6.9 Hz), 4.09(2H, q, J=6.9 Hz), 4.07(3H, s), 3.96(6H, s), 1.39 (3H, t, J=6.9 Hz), 1.27(3H, t, J=6.9 Hz).

REFERENCE EXAMPLE 12

(E)-1,3-Diallyl-8-(4-hydroxy-3,5-dimethoxystyryl)-7-methylxanthine (Compound m)

Melting Point:239.2°–239.8° C. (2-propanol/water) Elemental Analysis:$C_{22}H_{24}N_4 O_5$ Calcd. (%):C 62.25, H 5.70,N 13.20 Found (%):C 61.86, H 5.73,N 13.11 IR(KBr) vmax (cm⁻¹):1695, 1666, 1518, 1337, 1110. NMR (270 MHz; CDCl₃) δ(ppm):7.71(1H, d, J=15.8 Hz), 6.82(2H, s), 6.74(1H, d, J=15.8 Hz), 6.10–5.87(2H, m), 5.74(1H, brs), 5.35–5.16(4H, m), 4.76(2H, d, J=5.6 Hz), 4.65(2H, d, J=5.6 Hz), 4.06(3H, s), 3.96(6H, s).

REFERENCE EXAMPLE 13

(E)-1,3-Diethyl-8-(3-hydroxystyryl)-7-methylxanthine (Compound

Melting Point:250°–251° C. Elemental Analysis:$C_{18}H_{20}N_4 O_3 \cdot H_2 O$ Calcd. (%):C 60.35, H 6.19,N 15.63 Found (%):C 60.68, H 6.28,N 15.60 IR%(KBr) vmax (cm⁻¹):1763, 1714, 1670, 1632, 1586, 1518, 1422. NMR (270 MHz; DMSO-d₆) δ(ppm):9.55(1H, s), 7.55(1H, d, J=15.8 Hz), 7.22(1H, d, J=15.8 Hz), 7.13–7.25(3H, m), 6.79(1H, d, J=6.9 Hz), 4.06(2H, q, J=6.9 Hz), 4.01(3H, s), 3.90(2H, q, J=6.9 Hz), 1.26(3H, t, J=6.9 Hz), 1.13(3H, t, J=6.9 Hz).

REFERENCE EXAMPLE 14

(E)-1,3-Diethyl-8-(2-hydroxy-5-methoxystyryl)-7-methylxanthine Compound o)

Melting Point:248°–250° C. (N, N-dimethylformamide/water) Elemental Analysis:$C_{19}H_{22}N_4 O_4 \cdot H_2 O$ Calcd. (%):C 58.75, H 6.23,N 14.43 Found (%):C 58.81, H 6.62,N 14.54 IR(KBr) vmax (cm⁻¹):1616, 1559, 1527, 1449, 1419. NMR (270 MHz; DMSO-d₆) δ(ppm):9.63(1H, s), 7.93(1H, d, J=15.8 Hz), 7.33(1H, d, J=2.4 Hz), 7.28(1H, d, J=15.8 Hz), 6.83(1H, s), 6.81(1H, d, J=2.4 Hz), 4.07(2H, q, J=6.9 Hz), 4.01(3H, s), 3.91(2H, q, J=6.9 Hz), 3.75(3H, s), 1.26(3H, t, J=6.9 Hz), 1.13(3H, t, J=6.9 Hz).

REFERENCE EXAMPLE 15

(E)-1,3-Diethy 1-8-(2-hydroxy-3-methoxystyry 1)-7-methylxanthine (Compound p)

Melting Point:225.4°–226.4° C. (dioxane/water) Elemental Analysis:$C_{19}H_{22}N_4 O_4$ Calcd. (%):C 61.61, H 5.98,N 15.13 Found (%):C 61.40, H 6.12,N 15.09 IR(KBr) vmax (cm⁻¹):1758, 1721, 1507, 1328. NMR (270 MHz; DMSO-d₆) δ(ppm):9.26(1H,brs), 8.01(1H, d, J=16.2 Hz), 7.40(1H, d, J=7.9 Hz), 7.24(1H, d, J=16.2 Hz), 6.97(1H, d, J=7.9 Hz), 6.83(1H, d, J=7.9 Hz), 4.07(2H, q, J=6.9 Hz), 4.00(3H, s), 3.92(2H, q, J=6.9 Hz), 3.84(3H, s), 1.26(3H, t, J=6.9 Hz), 1.13(3H, t, J=6.9 Hz).

REFERENCE EXAMPLE 16

(E)-1,3-Diethyl-8-(2,3-dihydroxystyryl)-7-methylxanthine (Compound q)

Melting Point:242.2°–244.2° C. (dioxane/water) Elemental Analysis:$C_{18}H_{20}N_4O_4 \cdot 0.6\ H_2O$ Calcd. (%):C 58.88, H 5.82,N 15.26 Found (%):C 58.81, H 5.80,N 14.87 IR(KBr) vmax (cm⁻¹):1691, 1642, 1543, 1437, 1279. NMR (270 MHz; DMSO-d₆) δ(ppm):7.99(1H, d, J=15.8 Hz), 7.25(1H, d, J=7.6 Hz), 7.21(1H, d, J=15.8 Hz), 6.80(1H, d, J=7.6 Hz), 6.68(1H, t, J=7.6 Hz), 4.07(2H, q, J=6.9 Hz), 4.00(3H, s), 3.92(2H, q, J=6.9 Hz), 1.26(3H, t, J=6.9 Hz), 1.13(3H, t, J=6.9 Hz).

REFERENCE EXAMPLE 17

(E)-1,3-Diethyl-8-(3-hydroxy-4,5-methylenedioxystyryl)-7-methylxanthine (Compound r)

Substantially the same procedure as in Reference Example 1 was repeated using 500 mg (1.25 mmol) of (E)-1,3-diethyl-8-(3,4-methylenedioxy-5-methoxystyryl)-7-methylxanthine (Japanese Published Unexamined Patent Application No. 211856/94). The obtained crude product was purified by silica gel column chromatography to give 216 mg (45% yield) of Compound r as a yellow solid, which was finepowdered in ethanol to give yellow powders.

Melting Point:264.7°–268.2° C. Elemental Analysis:$C_{19}H_{20}N_4O_5 \cdot 0.6\ H_2O$ Calcd. (%):C 57.75, H 5.41,N 14.18 Found (%):C 57.90, H 5.60,N 13.95 IR(KBr) vmax (cm⁻¹):1714, 1657, 1537, 1460. NMR (270 MHz; DMSO-d₆) δ(ppm):9.85(1H, s), 7.47(1H, d, J=15.8 Hz), 7.12(1H, d, J=15.8 Hz), 7.05(1H, d, J=1.3 Hz), 6.75(1H, d, J=1.3 Hz), 6.02(2H, s), 4.06(2H, q, J=6.9 Hz), 4.00(3H, s), 3.91(2H, q, J=6.9 Hz), 1.25(3H, t, J=6.9 Hz), 1.12(3H, t, J=6.9 Hz).

PREPARATION EXAMPLE 1

Tablet

Tablets having the following composition are prepared according to a conventional method.

Prescription

| | |
|---|---|
| Compound 4 | 20 mg |
| Lactose | 143.4 mg |
| Potato starch | 30 mg |
| Hydroxypropyl cellulose | 6 mg |
| Magnesium stearate | 0.6 mg |
| | 200 mg |

PREPARATION EXAMPLE 2

Fine Granules

Fine granules having the following compositions are prepared according to a conventional method.

Prescription

| | |
|---|---|
| Compound 5 | 20 mg |
| Lactose | 655 mg |
| Corn starch | 285 mg |
| Hydroxypropyl cellulose | 40 mg |
| | 1,000 mg |

PREPARATION EXAMPLE 3

Capsules

Capsules having the following composition are prepared according to a conventional method.

Prescription

| | |
|---|---|
| Compound 4 | 20 mg |
| Avicel | 99.5 mg |
| Magnesium stearate | 0.5 mg |
| | 120 mg |

PREPARATION EXAMPLE 4

Injectable Preparations

An injectable preparation having the following composition is prepared according to a conventional method.

Prescription

| | |
|---|---|
| Compound 5 | 2 mg |
| Purified soybean oil | 200 mg |
| Purified yolk lecithin | 24 mg |
| Injectable glucose solution | 50 mg |
| Injectable distilled water | 1.72 ml |
| | 2.00 ml |

PREPARATION EXAMPLE 5

Syrup

Syrup having the following composition is prepared according to a conventional method.

Prescription

| | |
|---|---|
| Compound 4 | 20 mg |
| Refined sucrose | 30 mg |
| p-hydroxybenzoic ethyl ester | 40 mg |
| p-hydroxybenzoic propyl ester | 10 mg |
| Strawberry flavor | 0.1 ml |
| Water | 99.8 ml |
| | 100 ml |

EFFECT OF THE INVENTION

The present invention provides novel xanthine derivatives and pharmaceutically acceptable salts thereof which are useful for treatment or prevention of various kinds of diseases caused by hyperergasia of adenosine $A_2$ receptors (for example, Parkinson's disease, senile dementia, depression, asthma, and osteoporosis).

We claim:

1. A xanthine derivative represented by Formula (I) or its pharmaceutically acceptable salt:

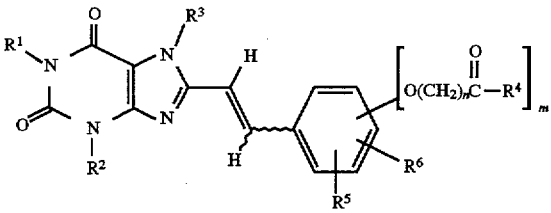

wherein $R^1$ and $R^2$ independently represent lower alkyl, lower alkenyl, or lower alkynyl; $R^3$ represents hydrogen, lower alkyl, lower alkenyl, or lower alkynyl; $R^4$ represents lower alkyl, or aryl which is optionally substituted with 1 to 4 substituents independently selected from the group consisting of lower alkyl, hydroxy, lower alkoxy, halogen, nitro, amino, lower alkylamino, di-lower alkylamino, benzyloxy, phenyl and phenoxy, wherein said lower alkyl substituent and lower alkoxy substituent are each optionally substituted with 1 to 3 substituents independently selected from the group consisting of halogen, nitro, lower alkoxy and amino; $R^5$ and $R^6$ independently represent hydrogen, lower alkyl, or lower alkoxy, or $R^5$ and $R^6$ are combined together to represent —O—$(CH_2)_p$—O— (where p is an integer of 1 to 3); n represents 0, 1 or 4; and m represents 1 or 2, with the proviso that $R^1$ and $R^2$ are not methyl.

2. A compound of claim 1 wherein $R^1$, $R^2$, and $R^3$ independently represent lower alkyl or lower alkenyl.

3. A compound of claim 1 wherein $R^3$ represents lower alkyl.

4. A compound of claim 3 wherein $R^1$ and $R^2$ independently represent ethyl, propyl or allyl.

5. A compound of claim 4 wherein $R^3$ represents methyl.

6. A compound of claim 5 wherein $R^4$ represents methyl, ethyl, tert-butyl or phenyl.

7. A compound of claim 6 wherein $R^5$ and $R^6$ independently represent hydrogen, methoxy, or $R^5$ and $R^6$ are combined together to represent —O—$CH_2$—O—.

8. A compound of claim 2, wherein $R^3$ represents lower alkyl.

9. A method for treatment of Parkinson's disease, comprising:

selecting a pharmaceutical composition containing at least one of the compounds of claims 1 to 7 or 8 and a pharmaceutically acceptable excipient; and administering said composition to a patient in need thereof.

10. A composition comprising at least one of the compounds of claims 1 to 7 or 8 and a pharmaceutically acceptable carrier.

11. A method of producing a pharmaceutical composition, comprising the steps of:

selecting a compound according to any of claims 1 to 7 or 8, and blending said compound with a pharmaceutically acceptable excipient.

12. A method of treating depression, comprising selecting a pharmaceutical composition containing at least one of the compounds of claims 1 to 7 or 8 and a pharmaceutically acceptable excipient; and administering said composition to a patient in need thereof.

* * * * *

UNITED STATES PATENT AND TRADEMARK OFFICE
CERTIFICATE OF CORRECTION

PATENT NO. : 5,703,085
DATED : December 30, 1997
INVENTOR(S) : FUMIO SUZUKI ET AL.

Page 1 of 3

It is certified that error appears in the above-identified patent and that said Letters Patent is hereby corrected as shown below:

COLUMN 14

Line 6, "category" should read --catalepsy--.

COLUMN 17

Line 30, "hexane/ethYl" should read --hexane/ethyl--.

COLUMN 18

Line 24, "(cm" should read --(cm$^{-1}$):--.
    Line 25, "1):1735," should read --1735,--.
    Line 39, "duck" should read --duct--.
    Line 43, "(cm" should read --(cm$^{-1}$):--.
    Line 44, "1):1693," should read --1693,--.
    Line 62, "(cm" should read --(cm$^{-1}$):--.
    Line 63, "1):1761," should read --1761,--.

COLUMN 19

Line 20, "(c$^{-1}$)" should read --(cm$^{-1}$)--.
    Line 47, "(cm" should read --(cm$^{-1}$):--.
    Line 48, "1):1688," should read --1688,--.

COLUMN 20

Line 1, "(cm" should read --(cm$^{-1}$):--.
    Line 2, "1):1764," should read --1764,--.
    Line 20, "(cm" should read --(cm$^{-1}$):--.
    Line 21, "1):1756," should read --1756,--.

UNITED STATES PATENT AND TRADEMARK OFFICE
CERTIFICATE OF CORRECTION

PATENT NO. : 5,703,085
DATED : December 30, 1997
INVENTOR(S) : FUMIO SUZUKI ET AL.

It is certified that error appears in the above-identified patent and that said Letters Patent is hereby corrected as shown below:

COLUMN 21

Line 42, "195.7°-196.320 C." should read --195.7°-196.3°C--.
    Line 64, "(cm⁻" should read --(cm$^{-1}$):--.
    Line 65, "1):1762," should read --1762,--.

COLUMN 24

Line 49, "(cm⁻" should read --(cm$^{-1}$):--.
    Line 50, "1):1680," should read --1680,--.

COLUMN 25

Line 37, "(cm⁻" should read --(cm$^{-1}$):--.
    Line 38, "1):1697," should read --1697,--.
    Line 61, "(cm⁻" should read --(cm$^{-1}$):--.
    Line 62, "1):1697," should read --1697,--.

COLUMN 26

Line 17, "(cm⁻" should read --(cm$^{-1}$):--.
    Line 18, "1):1693," should read --1693,--.
    Line 31, "Compound f)" should read --(Compound f)--.
    Line 47, "(cm⁻" should read --(cm$^{-1}$):--.
    Line 48, "1):1696," should read --1696,--.

UNITED STATES PATENT AND TRADEMARK OFFICE
CERTIFICATE OF CORRECTION

PATENT NO. : 5,703,085
DATED : December 30, 1997
INVENTOR(S) : FUMIO SUZUKI ET AL.

It is certified that error appears in the above-identified patent and that said Letters Patent is hereby corrected as shown below:

COLUMN 27

Line 50, "(Compound" should read --(Compound n)--.
Line 65, "Compound o)" should read --(Compound o)--.

COLUMN 32

Line 3, "comprising" should read --comprising:--.

Signed and Sealed this

Eighth Day of September, 1998

Attest:

BRUCE LEHMAN

Attesting Officer      Commissioner of Patents and Trademarks